(12) United States Patent (10) Patent No.: US 8,143,060 B2
Leese et al. (45) Date of Patent: Mar. 27, 2012

(54) METHOD OF ASSESSING THE VIABILITY OF THAWED DEVELOPMENTALLY COMPETENT EMBRYOS

(75) Inventors: Henry J. Leese, York (GB); Franchesca D. Houghton, Southampton (GB)

(73) Assignee: Novocellus Limited (GB)

( * ) Notice: Subject to any disclaimer, the term of this patent is extended or adjusted under 35 U.S.C. 154(b) by 493 days.

(21) Appl. No.: 12/162,284

(22) PCT Filed: Jan. 26, 2007

(86) PCT No.: PCT/GB2007/000277
§ 371 (c)(1),
(2), (4) Date: Oct. 7, 2008

(87) PCT Pub. No.: WO2007/085851
PCT Pub. Date: Aug. 2, 2007

(65) Prior Publication Data
US 2009/0239207 A1 Sep. 24, 2009

(30) Foreign Application Priority Data

Jan. 27, 2006 (GB) .................................. 0601746.1

(51) Int. Cl.
*A01N 1/00* (2006.01)
*C12Q 1/02* (2006.01)
*C12N 9/00* (2006.01)
*C12N 1/20* (2006.01)
*C07H 21/02* (2006.01)

(52) U.S. Cl. ............ 435/377; 435/1.1; 435/1.3; 435/29; 435/189; 435/252.3; 536/23.1

(58) Field of Classification Search ........................ None
See application file for complete search history.

(56) References Cited

U.S. PATENT DOCUMENTS 7,202,395 B2  4/2007 Leese et al.

FOREIGN PATENT DOCUMENTS

WO  WO 01/53518 A2  7/2001

OTHER PUBLICATIONS

Balen "GnRH Agonists and Superovulation for Assisted Contraception", *Infertility and Reproductive Medicine Clinics of North America* 12(1):89-104 (2001).
Brison et al. "Identification of viable embryos in IVF by non-invasive measurement of amino acid turnover", *Human Reproduction* 19(10):2319-2324 (2004).
Bourgain et al. "The emdometrium in stimulated cycles for IVF", *Human Reproduction Update* 9(6):515-522 (2003).
Devroey et al. "Reproductive biology and IVF: ovarian stimulation and endometrial receptivity", *TRENDS in Endocrinology and Metabolism* 15(2):85-90 (2004).
Dulioust et al. "Long-term effects of embryo freezing in mice", *Proc. Natl. Acad. Sci. USA* 92:589-593 (1995).
Edgar et al. "The application and impact of cryopreservation of early cleavage stage embryos in assisted reproduction", *Human Fertility* 8(4):225-230 (2005).
Edgar et al. "A quantitative analysis of the impact of cryopreservation on the implantation potential of human early cleavage stage embryos", *Human Reproduction* 15(1):175-179 (2000).
El-Toukhy et al. "Effect of blastomere loss on the outcome of frozen embryo replacement cycles", *Science Direct—Fertility and Sterility* 79(5):1106-1111 (2003).
Emiliani et al. "Comparison of ethylene glycol, 1,2-propanediol and glycerol for cryopreservation of slow-cooled mouse zygotes, 4-cell embryos and blastocysts", *Human Reproduction* 15(4):905-910 (2000).
Ho et al. "Preimplantation Development of Mouse Embryos in KSOM: Augmentation by Amino Acids and Analysis of Gene Expression", *Molecular Reproduction and Development* 41:232-238 (1995).
Houghton et al. "Metabolism and developmental competence of the preimplantation embryo", *Erupean Journal of Obstetrics & Gynecology and Reproductive Biology* 115S:S92-S96 (2004).
Houghton et al. "Non-invasive amino acid turnover predicts human embryo development capacity", *Human Reproduction* 17(4):999-1005 (2002).
Humpherson et al. "Amino acid metabolism of the porcine blastocyst", *Theriogenology* 64:1852-1866 (2005).
Kaidi et al. "Effect of Conventional Controlled-Rate Freezing and Vitrification on Morphology and Metabolism of Bovine Blastocysts Produced in Vitro", *Biology of Reproduction* 65:1127-1134 (2001).
Kowalik et al. "Comparison of clinical outcome after cryopreservation of embryos obtained from intracytoplasmic sperm injection and in-vitro fertilization", *Human Reproduction* 13(10):2848-2851 (1998).
Lane et al. "Understanding cellular disruptions during early embryo development that perturb viability and fetal development", *Reproduction, Fertility and Development* 17:371-378 (2005).
Lesny et al. "The junctional zone of the uterus and its contractions", *BJOG: an International Journal of Obstetrics and Gynaecology* 111:1182-1189 (2004).
Lukassen et al. "Hormonal stimulation for IVF treatment positively affects the $CD56^{bright}/CD56^{dim}$ NK cell ratio of the endometrium during the window of implantation", *Molecular Human Reproduction* 10(7):513-520 (2004).
Pal et al. "Postthaw blastomere survival is predictive of the success of frozen-thawed embryo transfer cycles", *Fertility and Sterility* 82(4):821-826 (2004).

(Continued)

*Primary Examiner* — Christian Fronda
(74) *Attorney, Agent, or Firm* — Myers Bigel Sibley & Sajovec, PA (57) ABSTRACT

The invention relates to a method of assessing the viability of a thawed cell wherein the cell is a gamete, an embryo, a karyoplast, a putative stem cell population, a stem cell precursor population or a stem cell population. The method includes incubating the thawed cell in a culture medium including a plurality of amino acids and determining the change in concentration in the medium of at least one amino acid.

8 Claims, 6 Drawing Sheets

OTHER PUBLICATIONS

Pegg "The role of vitrification techniques of cryopreservation in reproductive medicine", *Human Fertility* 8(4):231-239 (2005).

Rinaudo et al. "Effects of embryo culture on global pattern of gene expression in preimplantation mouse embryos", *Reproduction* 128:301-311 (2004).

Rizos et al. "Bovine Embryo Culture in the Presence or Absence of Serum: Implications for Blastocyst Development, Cryotolerance, and Messenger RNA Expression", *Biology of Reproduction* 68:236-243 (2003).

Tachataki et al. "Quantitative RT-PCR reveals tuberous sclerosis gene, TSC2, mRNA degradation following cryopreservation in the human preimplantation embryo", *Molecular Human Reproduction* 9(10):593-601 (2003).

Tay et al. "Human tubal fluid: production, nutrient composition and response to adrenergic agents", *Human Reproduction* 12(11):2451-2456 (1997).

Trounson "Preservation of human eggs and embryos", *Fertility and Sterility* 46(1):1-13 (1986).

Ubaldi et al. "Cumulative pregnancy rates after transfer of fresh and thawed embryos", *European Journal of Obstretics & Gynecology and Reproductive Biology* 115S:S106-S109 (2004).

Van der Elst et al. "Selective transfer of cryopreserved human embryos with further cleavage after thawing increases delivery and implantation rates", *Human Reproduction* 12(7):1513-1521 (1997).

International Search Report corresponding to International Application No. PCT/GB2007/000277 mailed Apr. 20, 2007.

METHOD OF ASSESSING THE VIABILITY OF THAWED DEVELOPMENTALLY COMPETENT EMBRYOS

RELATED APPLICATIONS

The present application is a 35 U.S.C. §371 national phase application of PCT International Application No. PCT/GB2007/000277, having an international filing date of Jan. 26, 2007 and claiming priority to Great Britain Patent Application No. 0601746.1, filed Jan. 27, 2006. The disclosure of each application is incorporated herein by reference in its entirety. The above PCT International Application was published in the English language and has International Publication No. WO 2007/085851A1.

FIELD OF THE INVENTION

This invention relates to a method of assessing the viability of a thawed cell.

In order to increase success rates during IVF the ovary is stimulated to produce more than one oocyte. As a consequence most IVF cycles result in a total number of embryos which exceeds the optimum for transfer to an individual patient in a single cycle. The ethical and economic solution to this problem is embryo cryopreservation. Embryo cryopreservation allows storage of good quality, supernumeracy embryos until they can be transferred in later cycles, thus decreasing the number of stimulated ovary drug treatment cycles needed for the attainment of pregnancy and therefore the risk of ovarian hyperstimulation syndrome (Trounson, 1986), and providing protection against multiple gestations. Cryopreservation also allows replacement of thawed embryos during spontaneous ovulatory cycles or cycles in which the estrogen and progesterone hormone levels do not exceed that which occurs naturally, thus increasing pregnancy rates per patient. Cryopreservation of pronucleate or early cleavage stage embryos is routinely offered in most assisted conception units.

Techniques of controlled-rate freezing are utilized that slowly cool embryos in cryoprotectant fluid, from body temperature down to −196° C. (where all cell processes stop), at which temperature they are stored in containers of liquid nitrogen. The cryoprotectant is used to protect the cell from damage. When the cells are to be thawed they are taken from liquid nitrogen, thawed, cryoprotectants removed and the cells cultured.

Several factors are associated with cooling and cryopreservation that lead to cell injury and compromise post-thaw function and development. Cell injury may be caused by intracellular ice formation and then rapid cooling of this intracellular ice; also extra-cellular ice formation leads to increased electrolyte concentrations in unfrozen sections, and cell dehydration. Dehydration and re-hydration induce mechanical stress on lipid membranes and cause physical deformities and changes in the phase behavior, detected using in vitro models of membrane solute interactions. These physical alterations may affect the cell at many levels: the cell membrane and cellular organelles may be altered; the zona pellucida, which surrounds the embryo, has been shown to suffer (a certain amount of) hardening during cryopreservation, and the spindle apparatus and hence chromosome separation may be damaged. Recently, certain genes have been shown to be induced by the freezing and thawing process, suggesting that the cell is actively responding to an insult. Slow freezing combined with cryoprotectants allows cells to be protected from the detrimental mechanisms noted above by decreasing intracellular ice and the effects of increasing solute concentrations. The extracellular ice drives the dehydration of the cell via an equilibrium process. A more rapid technique, vitrification, uses high levels of cryoprotectants and very rapid rates of cooling to minimize the formation of intracellular ice. It is a non-equilibrium technique.

Freezing and ice formation induce dehydration of the bi-lamellar (i.e. two-layered) lipid membrane. The liquid crystallization to gel phase transition with freezing results in an ordering of the phospholipid hydrocarbon tails into a more packed and parallel array which may lead to increased permeability to water and cations, segregation of integral membrane proteins, decreased activities of membrane bound enzymes, and decreased lateral diffusion of proteins. It is likely that spermatozoa and oocytes experience similar effects, though their lipid constitution is quite different. Mature oocytes have microtubules located at the meiotic spindle. Reducing the temperature to 25° C. for 10 minutes disrupts the microtubules and complete dissolution occurs at 0° C. Re-warming in the mouse leads to reconstitution of the microtubules, however this may not occur in humans due to deficiency of pericentriolar material needed to nucleate tubule polymerization. The resultant oocyte may be prone to aneuploidy (i.e. abnormal numbers of chromosomes) as a result of spindle disorganization. Freezing may also affect fertilization by decreasing cortical granules and the chymotrypsin sensitivity of the zona pellucida. The shell may, in effect, be too 'hard.' Using single cell gel electrophoresis Linford and Meyers showed that sperm DNA may be damaged. Mitochondria are also susceptible to cryopreservation damage. The degeneration of oocyte DNA during cryopreservation and subsequent culture appears to involve the process of apoptosis, with classic markers and caspases detected. Thus the cells are undergoing programmed cell death. It is of interest that genes involved with stress responses including heat shock proteins, oxidative stress scavengers, and enzymes involved with glucose metabolism, are also activated.

Although embryo cryopreservation is generally considered a safe procedure (Wood), controversy still remains regarding the long term safety of this technique (Winston and Hardy, 2002). This is largely a result of studies performed in the mouse, where it has been suggested that embryo freezing may affect metabolism in late preimplantation development (Emiliani et al., 2000) and have more subtle long term effects which are only manifested late in development (Dulioust et al. 1995). Freezing of human embryos has also been reported to alter gene expression profiles (Tachataki et al., 2003). These investigators found that day 2 frozen embryos contained less mRNA for the tuberous sclerosis gene, TSC2 than fresh day 2 embryos.

The primary concern with the use of cryopreservation techniques is the possible loss of embryos to cryoinjury, meaning some healthy embryos may not survive the stress of freezing and thawing. The exact number of embryos lost to cryoinjury varies, but it is very likely that freezing will cause loss of some embryos, perhaps as many as 25-50% of those cryostored. One interpretation of this is that cryopreservation may even act as a "selection gate" for the more viable embryos, though this has never been proven.

Another concern with cryopreservation is the potential risk of birth defects in children produced from frozen/thawed embryos. In the domestic animal industry, large-scale freezing and transfer of embryos has not resulted in increased birth defects. Studies to date on those human offspring arising from thawed embryos have not shown any significant increase in abnormalities when compared to pregnancy outcomes in the rest of the population.

Overall cryopreservation leads to a 30 to 40% reduction in implantation potential (Edgar et al., 2000 and 2005; El-Toukhy et al., 2003). Other studies have shown similar clinical pregnancy and implantation rates of frozen thawed embryos ranging from 10 to 30% and 5 to 15% (Van der Elst et al., 1997; Kowalik et al., 1998; Ubaldi et al., 2004). The reduced success rates of embryos transferred in frozen cycles is attributed to the fact that cryopreserved embryos additionally have to endure the freezing and thawing process which is generally perceived in the art to alter homeostasis, metabolism, cell integrity and developmental potential. It is known that metabolism is intrinsic to early embryo health and that metabolism is immediately perturbed when embryos are stressed (reviewed by Houghton and Leese, 2004; Lane and Gardner, 2005). One of the most significant factors limiting the success of cryopreservation is post thaw embryo survival due to the formation of ice crystals during the freezing process (Liebermann et al., 2002) which is thought to damage cell membranes and lead to blastomere lysis (Pal et al., 2004).

In consideration of the above it stands to reason that, although the first successful pregnancy after cryopreservation was reported in 1983, the procedure of cryopreservation remains relatively new and the long-term effects on the embryo and subsequent offspring are unknown. The major disadvantage of cryopreservation is that the success rate of establishing a pregnancy using frozen/thawed embryos is generally lower than in a "fresh cycle", with an overall 30 to 40% reduction in implantation potential. These differences indicate that freezing and thawing of the embryo can have a detrimental effect on the viability of an embyro. The length of time that a cryopreserved embryo may retain its viability when in the frozen state is also unknown.

Success in IVF is dependent on the selection of the best embryo being chosen for transfer into the uterus. Before a transfer, the embryos are thawed and each embryo will be examined to determine whether it is medically appropriate (a viable, normally developing embryo) to transfer. There is no exact test for embryo quality and the distinction of a "good quality embryo" is a subjective assessment. Embryos are currently selected using morphological criteria. Morphological assessment involves counting the number of cells in an embryo and establishing its 'Grade'; usually on a 1 to 4 or 1 to 5 scale. The measures of Grade and cell number may then be combined to give a 'score' for a particular embryo. Scoring embryos is a highly skilled business and takes the average Clinical Embryologist approximately 3 months to learn. The main problem with morphological assessment is the high degree of subjectivity that is involved. It does not provide a robust test of developmental potential since there is only a 23% average success rate per treatment cycle started (REF, HFEA). Among the potential reasons to explain this low rate despite the transfer of morphologically good embryos are endometrial receptivity (Bourgain and Devroey, 2003; Devroey et al., 2004; Lukassen et al., 2004) and a traumatic embryo transfer leading to increased junctional zone contractions (Reviewed by Lesny and Killick, 2004). There is a plethora of data demonstrating altered gene expression patterns of embryos cultured in different medium but which morphologically appear normal (Ho et al., 1995; Rizos et al., 2003; Rinaudo and Schultz, 2004; Lee et al., 2004). Hence embryos may have normal morphology but possess alterations in their biochemistry making it currently impossible for embryologists to choose the absolute best embryo to transfer.

Only about 50% of frozen embryos, after microscopic analysis, are satisfactory for transfer. It is thought that those that do not survive the cryopreservation and thawing process may have been produced from less viable oocytes or sperm. The actual cycle of the transfer process of frozen embryos is identical to that of "fresh" embryos obtained in the IVF cycle.

Co-pending patent application WO01/53518 shows that amino acid depletion/appearance ('turnover') during cleavage predicts the ability of spare 'fresh' human embryos to develop to the blastocyst stage in vitro (Houghton et al., 2002) and to give rise to a pregnancy and live offspring following transfer (Brison et al., 2004). These findings are consistent with the general theory that developmental competency is determined early in development and that perturbations during the early stages of preimplantation development may have long-term implications.

Because of the practical advantages that the technique of cryopreservation can offer to assisted contraception, there is a need to assess reliably the developmental capacity of an egg or embryo post-thaw.

Cryopreservation is not a benign process and many of the functions of the cell may be affected. The selection criteria for embryos which have been subjected to the cyropreservation process are therefore different from those employed in the selection of 'fresh' embryos. Embyros that have been frozen are generally slower-growing and therefore morphologically very different from fresh embryos. The need for effective parameters for selecting the best embryos is paramount when a large number of them are available for transfer. Implanting multiple embryos has led to an unacceptably high rate of multiple births. As the aim of assisted conception is to produce a healthy baby, reducing multiple pregnancy rates is a major goal and transferring a single embryo is the ideal. The ability to identify embryos with high implantation potential will allow more effective selection of embryos for embryo transfer and reduce the likelihood of multiple pregnancy without reducing overall pregnancy rates. The need for effective parameters for selecting thawed embryos with the best potential to develop to term is paramount.

STATEMENTS OF THE INVENTION

According to the present invention there is provided a method of assessing the viability of a thawed cell wherein said cell is a gamete, an embryo, a karyoplast, a putative stem cell population, a stem cell precursor population or a stem cell population, said method comprising incubating the thawed cell in a culture medium including a plurality of amino acids and determining the change in concentration in the medium of at least one amino acid.

Surprisingly it has been found that the post-thaw metabolism of single human embryos in terms of amino acid turnover can be used to predict developmental capacity to the blastocyst stage.

The method of the invention is equally applicable to other mammalian species such as bovine and porcine. Cattle embryos are a good model for the human: Cattle are normally monovulators, as are humans. Cattle embryos are also about the same diameter as human embryos (~140µ) and have a broadly similar pattern of energy metabolism, measured as oxygen, pyruvate and glucose consumption and/or lactate production. Approximately the same proportion of in vitro-produced (IVP) cattle zygotes reach the blastocyst stage in vitro (20-40%) as in the human (20-50%) and zygotic genome activation is initiated at closely related stages (4-8 cell in the human; 8-16 cell stage in the cow). The profile of amino acid metabolism by porcine blastocysts is qualitatively and quantitatively similar to that given by human embryos during the morula:blastocyst transition, suggesting that the porcine blastocyst is also good model for the human.

Equally the methods are readily applicable to different cell types, e.g., gamete (at any stage of development), karyoplast, a putative stem cell population, a stem cell precursor population or a stem cell population. These cell types can all be frozen and the general principles of the invention apply. The term viability is used in its broadest sense to encompass, amongst other things, the development of an embryo to the blastocyst stage, successful implantation of an embryo and pre-implantation screening methods.

In one embodiment of the invention, the method comprises the step of selecting said thawed cell for further development if the change meets a predetermined criterion. Preferably the predetermined criterion is an increase or decrease in at least one amino acid.

Preferably the culture medium comprises Earle's Balanced Salt Solution supplemented with glucose, L-lactate, pyruvate and a physiological mixture of amino acids. Preferably the concentration of amino acids in the spent medium is measured using HPLC followed by derivatisation with o-phthaldialdehyde.

In one embodiment of the method an amino acid consumption or production profile is generated. Preferably the amino acid consumption or production profile is used as a whole as a selection marker in assessing the viability of a thawed cell. In one embodiment of the invention, selection of the most viable thawed cell is based upon a group of amino acids, typically comprising two to seven amino acids, whose consumption or production profile is indicative of a healthy, developing thawed cell for that species. Alternatively selection of the most viable thawed cell is based upon a single amino acid, whose consumption or production profile is indicative of a healthy developing thawed cell for that species.

Preferably the thawed cell is derived from any organism including humans, cows, pigs, sheep, any domestic animal or a rare and threatened species. In a preferred embodiment the method is used for humans.

Preferably the amino acid used for a selection marker includes one or a combination of glutamate, glutamine, glycine, arginine, alanine, lysine.

Preferably the method involves assessing the ability of a thawed mammalian pre-implantation embryo to develop to a blastocyst stage and/or be successfully implanted said method comprising:
(i) incubating the thawed mammalian pre-implantation embryo in a culture medium comprising a plurality of amino acids and;
(ii) determining an increase and/or decrease in concentration of at least one amino acid in the culture medium to determine amino acid turnover, wherein a thawed mammalian pre-implantation embryo with a lower range of amino acid turnover is associated with development to the blastocyst stage and/or successful implantation.

Preferably the method further comprises the step of selecting said thawed mammalian pre-implantation embryo for further development to the blastocyst stage and/or implantation.

Preferably the ability of the thawed mammalian pre-implantation embryo to develop to the blastocyst stage and/or be successfully implanted is achieved in 24 hours, 10 hours, 6 hours or less after transfer of the thawed mammalian pre-implantation embryo into the culture medium.

Preferably the method is used to assess the ability of the thawed mammalian pre-implantation embryo to implant and give rise to a clinical pregnancy. Clinical pregnancy following embryo transfer is detected by serum hCG 15 days post implantation and confirmed by the presence of a fetal heart at 5 weeks (Brison et al., 2004).

Preferably the thawed mammalian pre-implantation embryo is assessed from day 1 up to day 4 of development.

In one embodiment of the invention the method further comprises selecting the thawed implantation embryo based on the amino acid profile and introducing the selected thawed mammalian pre-implantation embryo into the uterine tract of an organism.

In one embodiment of the invention the thawed mammalian pre-implantation embryo is a mammalian pre-implantation embryo derived from an in-vitro matured egg. Alternatively the thawed mammalian pre-implantation embryo is a mammalian pre-implantation embryo derived from an in-vivo matured egg.

In one embodiment of the invention the thawed mammalian pre-implantation embryo has been produced by intra cytoplasmic sperm injection (ICSI).

In one embodiment of the invention the method involves determining the increase and/or decrease in concentration of at least one amino acid comprises utilizing a group of amino acids comprising two to seven amino acids, whose amino acid turnover is indicative of the ability of the thawed mammalian pre-implantation embryo to develop to the blastocyst stage and/or be successfully implanted for that species.

Accordingly the invention provides a method of assessing the ability of a thawed mammalian pre-implantation embryo to develop to a blastocyst stage and/or be successfully implanted, said method comprising incubating a single thawed mammalian pre-implantation embryo in a culture medium comprising a plurality of amino acids and determining the change in concentration in the culture medium of at least one amino acid, wherein the change in concentration is indicative of the ability of the thawed mammalian pre-implantation embryo to develop to the blastocyst stage and/or be successfully implanted.

The present invention also provides a method to differentiate between developmentally competent and arresting grade I embryos comprising incubating a grade I embryo in a culture medium including a plurality of amino acids and determining the change in concentration in the medium of at least one amino acid.

DETAILED DESCRIPTION OF THE INVENTION

The invention is described by way of example only and with reference to the accompanying drawings.

METHODS

Spare, frozen human embryos donated to research with informed patient consent were obtained from patients undergoing In Vitro Fertilisation (IVF) at the Assisted Conception Unit at St James's Hospital, Leeds. Full ethical approval for this work was granted by the Human Fertilisation and Embryology Authority (HFEA) as well as the Ethics Committees of the collaborating institutions.

Ovarian stimulation and oocyte collection were performed as previously described (Balen, 2001). In general, a long pituitary desensitisation protocol was used, with intranasal nafarelin followed by gonadotrophin stimulation with either human menopausal gonadotrophins (hMG, Menogon, Ferring Pharmaceuticals Ltd) or recombinant FSH (Puregon, Organon Laboratories Ltd). Briefly, oocytes were collected by follicular aspiration 36 h after hCG administration and cultured at 37° C. in 5% $CO_2$ in Medi-Cult IVF Medium under oil (Medi-Cult). The oocyte-cumulus complexes were inseminated with a final concentration of 70,000 motile sperm per ml at approximately 40 h post hCG and incubated overnight until fertilisation was confirmed by the presence of two pronuclei (day 1 post-insemination). Prior to being used for research, zygotes were cultured in 70 µl drops of Medi-Cult IVF medium under oil as above. A maximum of 3 embryos were transferred on day 2 post-insemination and any remaining embryos frozen and stored in liquid nitrogen for potential future use. According to HFEA guidelines, embryos may only be stored for 5 years and hence patients were contacted on a yearly basis to assess whether they wished their embryos to remain in storage, be discarded or donated to research. Those embryos donated to research were transported to York in a dry shipper for use in this study.

Embryos were thawed using the Sydney IVF thawing kit (Cook, Queensland, Australia) and placed into 10 µl drops of EBSS culture medium supplemented with 0.5% HSA, 1 mM glucose, 0.47 mM pyruvate, 5 mM lactate and a close to physiological mixture of amino acids (Tay et al., 1997) under mineral oil for approximately 3 h. Each patient's embryos were randomised between treatment groups and the developmental grade and stage of the embryos assessed (Houghton et al., 2002). The embryos were then cultured individually for 24 h, from day 2 to day 3 in 4 µl drops of the same medium in a humidified atmosphere containing 5% $CO_2$ and either 20% or 5% $O_2$ in air at 37° C. After incubation, embryo morphology was assessed, and the embryos placed individually into 10 µl drops of pre-equilibrated medium and incubated under either 5% or 20% $O_2$ until day 5 of development. The spent medium was stored at −80° C. Developmental stage and grade were again assessed before the embryos were placed individually into a 4 µl drop of pre-equilibrated medium under either 5 or 20% $O_2$ for 24 h, until day 6 of development. Embryo developmental stage and grade were assessed before removal from the drops. The spent medium was stored at −80° C.

Amino Acid Analysis

Embryo-free control drops were incubated in the same dish as those containing embryos to allow for any non specific changes in amino acid concentration throughout the culture period. The spent media were thawed and 2 µl aliquots diluted with 23 µl HPLC grade water. Amino acid analysis was performed by reverse-phase HPLC using a Kontron 500 attached to a Jasco F920 fluorescence detector and a 4.5×250 mm Hypersil ODS-16 column (Jones Chromatography) as previously described (Houghton et al., 2002). Briefly, derivatization was achieved by the automated reaction of 25 µl sample with an equal volume of reagent (10 µl 2mercaptoethanol and 5 ml o-phthaldialdehyde (OPA) reagent). The elution gradient operated at a flow rate of 1.3 ml per minute. Solvent A consisted of 18 ml tetrahydrofuran (Fisher Chemicals), 200 ml methanol and 800 ml sodium acetate (83 mmol/l, pH 5.9). Solvent B consisted of 800 ml methanol and 200 ml sodium acetate (83 mmol/l, pH 5.9). Using this method it was not possible to detect proline and cysteine.

Statistical Analysis

All data were analysed to determine whether they were normally distributed, using the Anderson-Darling normality test. Data for amino acid depletion/appearance were tested for significance from zero using either a 1-sample t-test or 1 sample Wilcoxon test, depending on whether the data were normally distributed. Differences between amino acid profiles for arresting and developing embryos were analysed using either a Student's t-test or Mann-Whitney U test. Differences between amino acid depletion, appearance, turnover and balance were analysed by Student's t-test.

Results

Amino Acid Turnover by Thawed Embryos from Day 2 to Day 3

Figure 1:
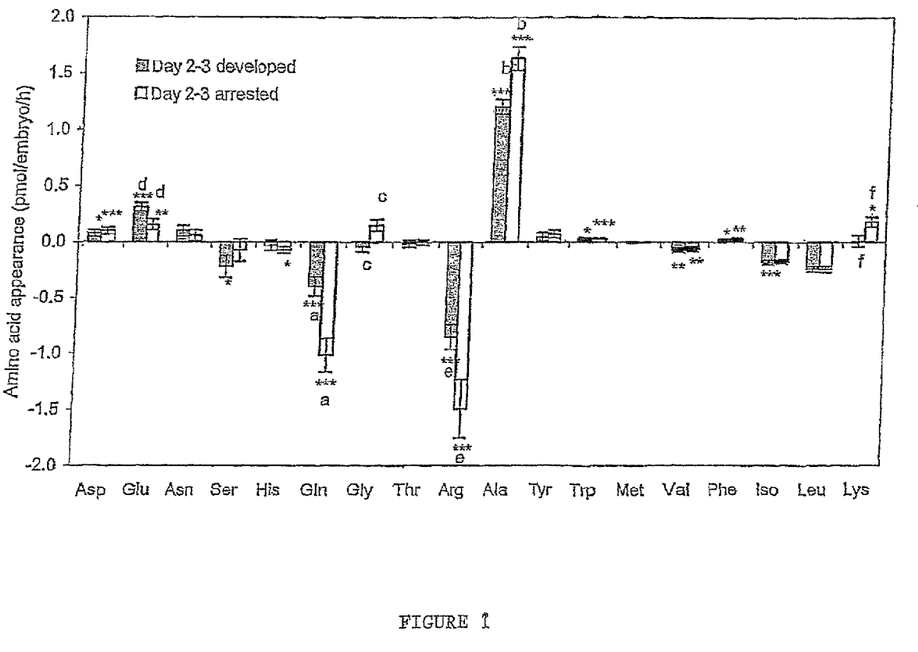
FIG. 1 Amino acid depletion and appearance by frozen thawed human embryos from day 2 to day 3 of development. n=21 for embryos which developed to the blastocyst stage and n=25 for embryos which arrested prior to the blastocyst stage. *P<0.05; P<0.01; *P<0.001 significance from zero. Bars with the same superscript are significantly different; a and b, P=0.001; c, P=0.0025; d P=0.016; e, P=0.032; f, P=0.0448.

Serine, glutamine, arginine, valine, isoleucine and leucine were significantly depleted from the medium (FIG. 1), while aspartate, glutamate, asparagine, alanine, tryptophan and phenylalanine appeared. Thawed embryos which subsequently failed to develop to the blastocyst stage consumed glutamine, arginine, valine, isoleucine and leucine and produced aspartate, glutamate, glycine, alanine, tyrosine, tryptophan, phenylalanine and lysine. There was a significant difference in the utilisation of glutamine (P=0.001), alanine (P=0.001), glycine (P=0.0025), glutamate (P=0.016), arginine (P=0.032) and lysine (P=0.0448) between those thawed embryos which developed to the blastocyst stage and those which arrested prior to blastocyst formation (FIG. 1).

Surprisingly, the cohort of frozen/thawed day 2 to 3 embryos that subsequently failed to develop to the blastocyst stage contained more grade I embryos than those which developed (Table 1) but there was no difference in the average number of blastomeres per embryo between grade I embryos which subsequently developed to the blastocyst or that arrested prior to blastocyst formation. Similarly, there was no difference between the total average blastomere number between the two groups (Table 1).

Figure 2:
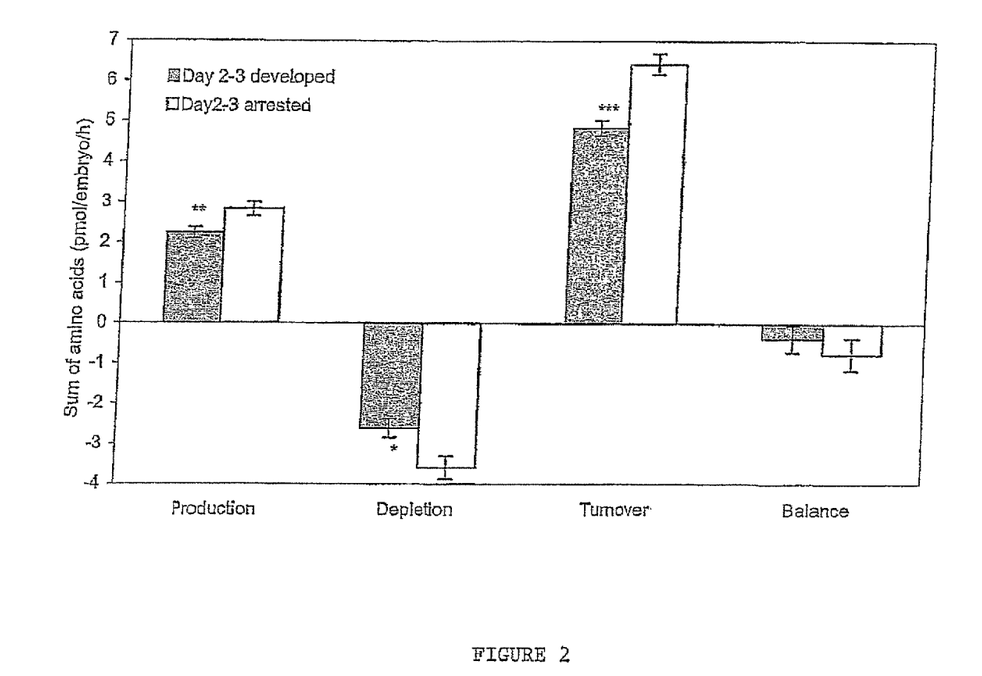
FIG. 2 Total amino acid production, depletion, turnover and balance by frozen thawed human embryos from day 2 to day 3 of development. *P<0.05; P<0.01; *P<0.001 significantly different from embryos which arrest.
Figure 3:
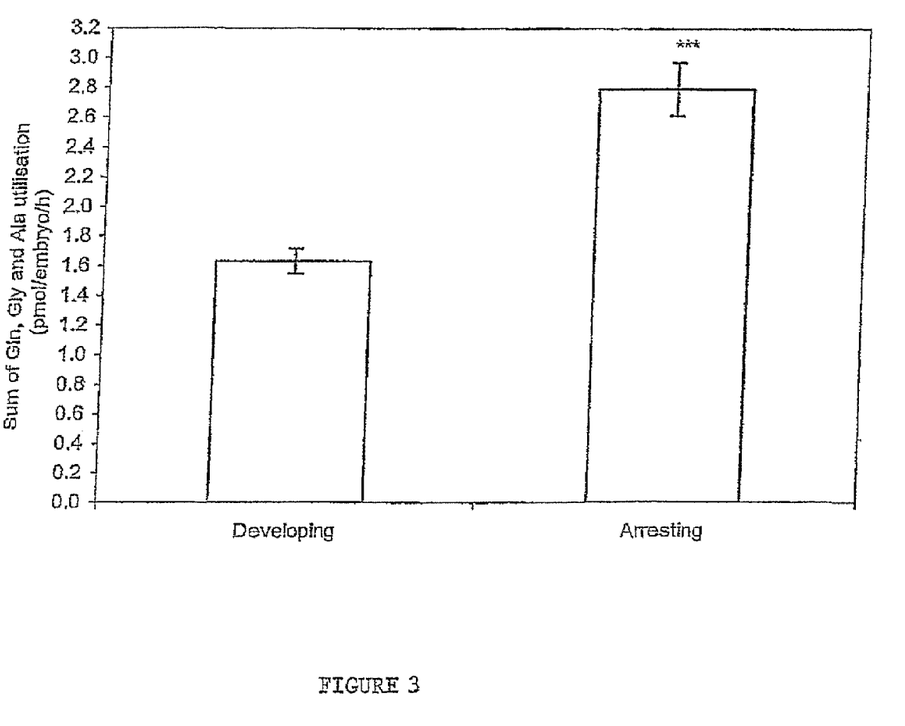
FIG. 3 Sum of glutamine, glycine and alanine utilisation by frozen thawed human embryos from day 2-day 3 of development. ***P<0.001 significantly different to embryos that develop.

Overall, embryos that arrested prior to the blastocyst stage were metabolically more active in terms of amino acid turnover, depleting (P=0.011) and producing (P=0.009) significantly more amino acids than their developing counterparts (FIG. 2). Interestingly it was found that developing embryos were balanced in terms of their amino acid turnover i.e., the amount depleted equalled that produced, whereas arresting embryos had a negative balance i.e., depleted more amino acids from the medium than they produced (FIG. 2). There was a significant difference (P<0.001) in the sum of glutamine, glycine and alanine from day 2 to day 3 between those embryos that developed to the blastocyst stage and those which arrested prior to blastocyst formation (FIG. 3).

Figure 4:
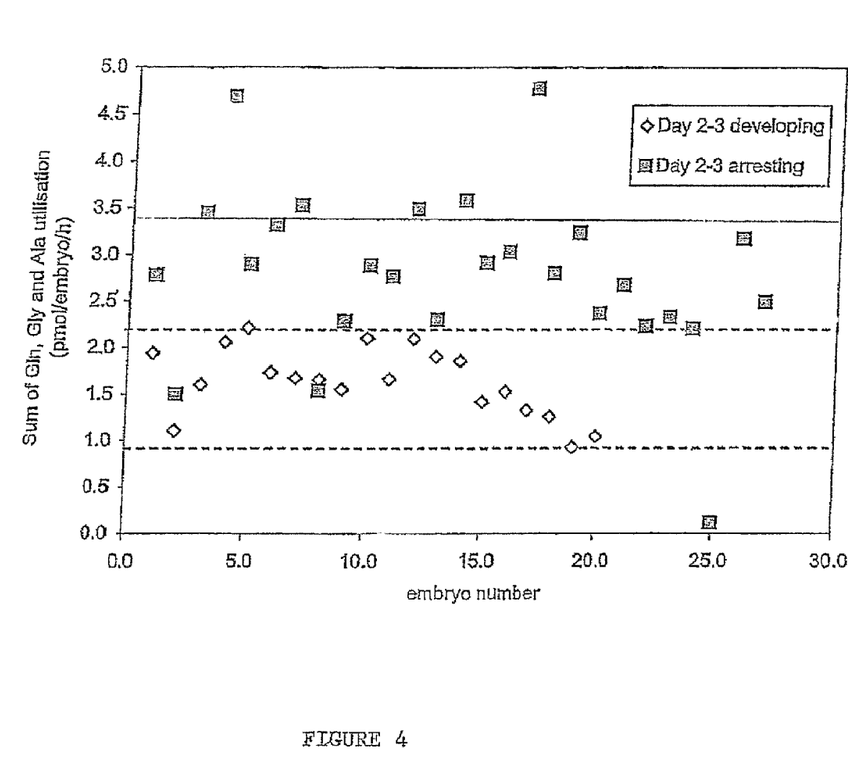
FIG. 4 Sum of glutamine, glycine and alanine for individual frozen thawed embryos which subsequently arrested or developed to blastocyst stage.

Using the sum of glutamine, glycine and alanine for individual embryos, it was possible to predict with 91% accuracy which embryos would develop to the blastocyst stage (FIG. 4).

Figure 5:
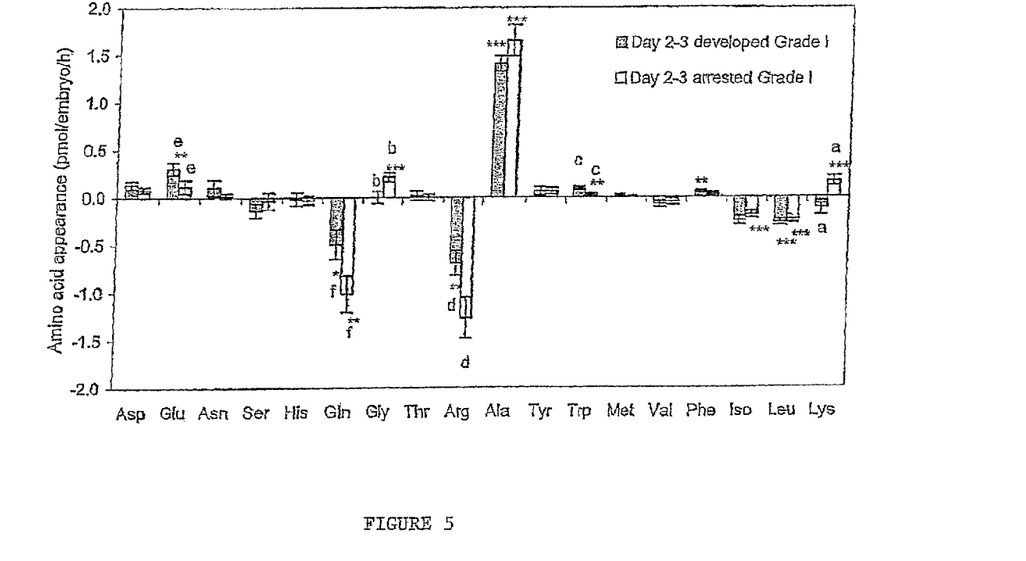
FIG. 5 Amino acid depletion and appearance by grade I thawed human embryos from day 2 to day 3 of development. n=6 for embryos which developed to the blastocyst stage and n=13 for embryos which arrested prior to the blastocyst stage. *P<0.05; P<0.01; *P<0.001 significance from zero. Bars with the same superscript are significantly different; a, P=0.014; b, P=0.024; c, P=0.029; P=0.035; e, P=0.0493; f, P=0.050.
Figure 6:
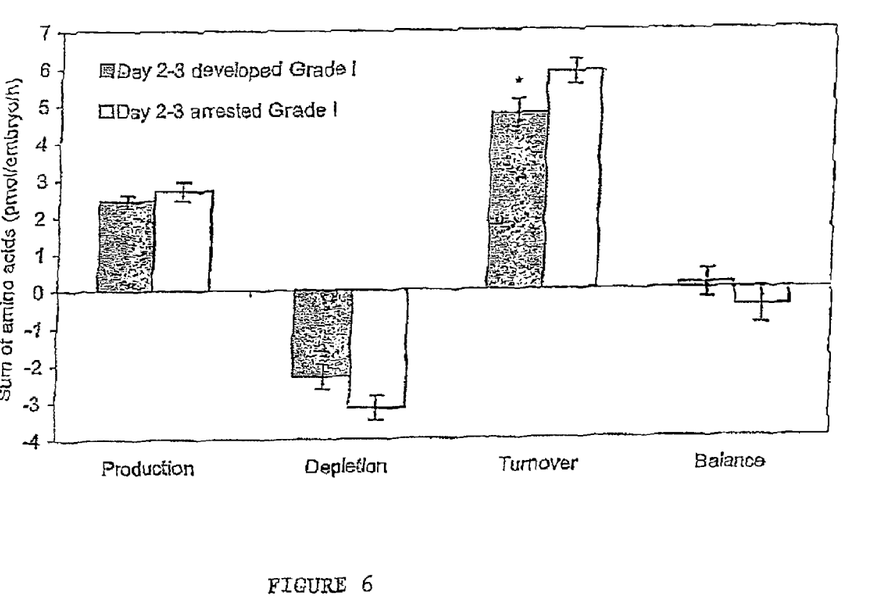
FIG. 6 Total amino acid production, depletion, turnover and balance by grade I thawed human embryos from day 2 to day 3 of development. *P<0.05 significantly different from embryos which arrest.

When the amino acid profile of grade I embryos was determined, there was a significant difference in amino acid depletion/appearance between those embryos which subsequently developed to the blastocyst stage compared with those grade I embryos which arrested prior to blastocyst formation (FIG. 5). Specific differences between the two groups were in the utilisation of lysine (P=0.014), glycine (P=0.024), tryptophan (P=0.029), arginine (P=0.035), glutamate (P=0.0493) and glutamine (P=0.050). It should be noted that there was no significant difference in the average number of blastomeres between grade I arresting and developing embryos (Table 1). Grade I embryos displayed no significant difference in total amino acid depletion, appearance or in the balance of amino acids (FIG. 6). However, arresting grade I embryos were metabolically more active in terms of amino acid turnover than those that developed to the blastocyst stage.

TABLE 1

Distribution of grades and average blastomere number for embryos post-thaw

| Thawing Grade | Number of embryos | |
|---|---|---|
| | Developed | Arrested |
| Grade I | 6 | 13 |
| Grade II | 9 | 9 |
| Grade II.5 | 6 | 2 |
| Grade III | 0 | 1 |
| Average blastomere number | 3.76 ± 0.53 | 3.12 ± 0.25 |
| Average Grade I blastomere number | 2.67 ± 0.62 | 3.00 ± 0.28 |

Discussion

The metabolism of frozen thawed human embryos from day 2 to day 3 has been determined in terms of amino acid depletion from, and appearance in the culture medium and used to predict their capacity to develop to the blastocyst stage. This is the first study to investigate the energy metabolism of cryopreserved human embryos. The amino acid profiles obtained can be used to predict which thawed embryo will develop to the blastocyst stage; a phenomenon which is independent of embryo grade and blastomere number on day 2. Those embryos with the ability to develop to the blastocyst stage are metabolically more quiet, having a lower rate of amino acid production, depletion and turnover than arresting embryos.

Amino acid profiling of cryopreserved embryos will also be able to predict implantation and live offspring similar to the study by Brison et al. (2004). These investigators used retrospective analysis of amino acid profiles of ICSI embryos measured from day 1 to day 2 of development. The embryos were selected for transfer on day 2, based on morphology alone and it was found that the turnover of asparagine, glycine and leucine were correlated with a clinical pregnancy. Specifically they were also independent of known predictors such as female age, basal FSH levels, embryo cell number and grade.

The technique provides a sensitive method which can readily be translated into IVF clinics and used by embryologists to select developmentally competent thawed embryos for transfer. The use of amino acid profiling has proved efficient not only in the retrospective selection of which frozen thawed embryo will develop to the blastocyst stage but also by providing the embryologist with a tool with which to distinguish between a population of the best grade I embryos in terms of developmental potential.

References

Balen A H (2001). GnRH agonists and superovulation for assisted conception. Infertility and Reproductive Medicine Clinics of North America 12, 89-104.

Bourgain C and Devroey, P (2003). The endometrium in stimulated cycles for IVF. Human Reproduction Update 9, 515-22.

Brison D R, Houghton F D, Falconer D et al (2004). Identification of viable embryos in IVF by non-invasive measurement of amino acid turnover. Human Reproduction 19, 2319-2324.

Devroey P, Bourgain C, Macklon N S and Fauser B C (2004). Reproductive biology and IVF: ovarian stimulation and endometrial receptivity. Trends in Endocrinology and Metabolism. 15, 84-90.

Dulioust E, Toyama K, Busnel M C et al (1995). Long-term effects of embryo freezing in mice. Proceedings of the National Academy of Sciences USA., 92, 589-93.

Edgar D H, Bourne H, Speirs A L and McBain JC (2000). A quantitative analysis of the impact of cyropreservation on the implantation potential of human early cleavage stage embryos. Human Reproduction 15, 175-179.

Edgar, DH, Archer J and Bourne H (2005). The application and impact of cryopreservation of early cleavage stage embryos in assisted reproduction. Human Fertility 8, 225-230.

El-Toukhy T, Khalaf Y, Al-Darazi K et al (2003). Effect of blastomere loss on the outcome of frozen embryo replacement cycles. Fertility and Sterility 79, 1106-1111.

Emiliani, S, Van den Bergh M, Vannin A-S, Biramane J and Englert Y (2000). Comparison of ethylene glycol, 1,2-propanediol and glycerol for cryopreservation of slow-cooled mouse zygotes, 4-cell embryos and blastocysts. Human Reproduction, 15, 905-910.

Ho, Y, Wrigglesworth K, Eppig J J and Schultz R M (1995). Preimplantation development of mouse embryos in KSOM: augmentation by amino acids and analysis of gene expression. Molecular Reproduction and Development 41, 232-238.

Houghton F D, Hawkhead J A, Humpherson P G et al (2002). Non-invasive amino acid turnover predicts human embryo developmental capacity. Human Reproduction 17, 999-1005. [Corrigenda (2003) Human Reproduction 18, 1756-1757]

Houghton F D and Leese H J (2004). Metabolism and developmental competence of the preimplantation embryo. European Journal of Obstetrics and Gynecology and Reproductive Biology 115S S92-S96.

Kowalik K, Palermo D G, Barmat L et al. (1998). Comparison of clinical outcome after cryopreservation of embryos obtained from intracytoplasmic sperm injection and in-vitro fertilization. Human Reproduction, 10, 2848-2851.

Lane M and Gardner D K (2005). Understanding cellular disruptions during early embryo development that perturb viability and fetal development. Reproduction Fertility and Development 17, 371-378.

Lesny P and Killick S R (2004). The junctional zone of the uterus and its contractions. British Journal of Obstetrics and Gynaecology 111, 1182-9.

Lukassen H G, Schonbeck Y, van Lierop M J et al (2004). Hormonal stimulation for IVF treatment positively affects the CD56bright/CD56dim NK cell ratio of the endometrium during the window of implantation. Molecular Human Reproduction 10, 513-20.

Pal L, Kovacs G, Witt B et al (2004). Postthaw blastomere survival is predictive of the success of frozen-thawed embryo transfer cycles. Fertility and Sterility 82, 821-826.

Pegg D E (2005) The role of vitrification techniques of cryopresevation in reproductive medicine. Human Fertility 8, 231-239

Rinaudo, P and Schultz R M (2004). Effects of embryo culture on global pattern of gene expression in preimplantation mouse embryos. Reproduction. 128, 301-311.

Rizos D, Gutierrez-Adan A, Perez-Gamelo S et al (2003). Bovine embryo culture in the presence or absence of serum: implications for blastocyst development, cryotolerance, and messenger RNA expression. Biology of Reproduction 68, 236-243.

Tachataki, M, Winston R M and Taylor D M (2003). Quantitative RT-PCR reveals tuberous sclerosis gene, TSC2, mRNA degradation following cryopreservation in the human preimplantation embryo. Molecular Human Reproduction 10, 593-601.

Tay J I, Rutherford A J, Killick S R et al (1997). Human tubal fluid: production, nutrient composition and response to adrenergic agents. Human Reproduction 12, 2451-2456.

Trounson A (1986). Preservation of human eggs and embryos. Fertility and Sterility 46, 1-12.

Ubaldi, F, Rienzi L, Baroni E et al (2004).

Cumulative pregnancy rates after transfer of fresh and thawed embryos. European Journal of Obstetrics, Gynecology and Reproductive Biology, 115 Suppl 1:S106-9.

Van der Elst, J, Van den Abbeel E, Vitrier S et al (1997). Selective transfer of cryopreserved human embryos with further cleavage after thawing increases delivery and implantation rates. Human Reproduction 7, 1513-1521.

Winston R M L and Hardy K (2002) Are we ignoring potential dangers of in vitro fertilization and related treatments? Nature Cell Biology 4 (S1) S14-S18.

The invention claimed is:

1. A method for differentiating between developmentally competent and arresting Grade I embryos, said method comprising:
   (i) incubating a Grade I embryo in a culture medium comprising a plurality of amino acids;
   (ii) determining an increase or decrease in concentration of at least one amino acid in the culture medium to determine amino acid turnover, wherein said at least one amino acid is selected from the group consisting of alanine, arginine, glutamine, glycine, glutamate, tryptophan and lysine, as compared to pre-culture medium; and
   (iii) selecting a developmentally competent Grade I embryo in the culture medium of step (ii),
   wherein said culture medium has a higher or lower concentration of at least one of said at least one amino acids, and wherein a lower amino acid turnover of said at least one amino acids is associated with the developmentally competent Grade I embryo of step (iii) and said developmentally competent Grade I embryo has an increased possibility of development to the blastocyst stage and/or successful implantation.

2. The method of claim 1 further comprising selecting the Grade I embryo for further development if the change meets a predetermined criterion, wherein the predetermined criterion comprises an increase or decrease in at least one amino acid.

3. The method of claim 1, wherein an amino acid consumption or production profile is generated which measures a change in concentration of at least one amino acid.

4. The method of claim 3, wherein said amino acid consumption or production profile is used as a selection marker in assessing the viability of a developmentally competent Grade I embryo.

5. The method of claim 3, wherein the amino acid consumption or production profile comprises consideration of amino acids selected from the group consisting of lysine, glycine, tryptophan, arginine, glutamate and glutamine.

6. The method of claim 1, wherein the developmentally competent Grade I embryo is derived from a mammal selected from the group consisting of humans, cows, pigs and sheep.

7. The method of claim 6, wherein the developmentally competent Grade I embryo is derived from a human.

8. The method of claim 6, wherein the developmentally competent Grade I embryo is derived from a cow.

* * * * *